United States Patent [19]
Burstein

[11] Patent Number: 6,162,829
[45] Date of Patent: Dec. 19, 2000

[54] (3R,4R)-$\Delta^8$-TETRAHYDROCANNABINOL-11-OIC ACIDS USEFUL AS ANTIINFLAMMATORY AGENTS AND ANALGESICS

[75] Inventor: Sumner H. Burstein, Framingham, Mass.

[73] Assignee: Atlantic Pharmaceuticals, Inc., Raleigh, N.C.

[21] Appl. No.: 08/953,765

[22] Filed: Oct. 17, 1997

[51] Int. Cl.[7] ............................ C07C 61/00; A61K 31/19
[52] U.S. Cl. ........................ 514/570; 514/557; 562/469
[58] Field of Search ............................ 562/469; 514/557, 514/784

[56] References Cited

U.S. PATENT DOCUMENTS

| | | | |
|---|---|---|---|
| 4,284,829 | 8/1981 | Althuis et al. | 568/764 |
| 4,371,720 | 2/1983 | Johnson et al. | 568/731 |
| 4,391,827 | 7/1983 | Harbert et al. | 424/331 |
| 4,831,059 | 5/1989 | Johnson et al. | 514/690 |
| 4,847,290 | 7/1989 | Burstein | 514/454 |
| 4,876,276 | 10/1989 | Mechoulam et al. | 514/454 |
| 4,921,994 | 5/1990 | Johnson et al. | 558/426 |
| 4,973,603 | 11/1990 | Burstein | 514/454 |
| 5,338,753 | 8/1994 | Burstein et al. | 514/454 |
| 5,605,928 | 2/1997 | Mechoulam et al. | 514/454 |

OTHER PUBLICATIONS

Blanc, et al., (CA 119:219267 abstract of Clin. Chem. (Washington D. C.), (1993), 39(8), 1705–12.

Jones et al. (CA 102:41075 abstract of J. Anal. Toxicol. (1984), 8(6), 252–4.

Defaye, Genevieve, (CA 72:79254 abstract of Publ. Sci. Tech. Min. Air (Fr.), Notes Tech. (1969), No. N.T. 165, 78 pages).

Matsumoto et al. (CA 77:126882 abstract of Chem. Lett. (1972), (7), 581–6.

Blanc, et al., (CA 119:219267 abstract of Clin. Chem. (Washington D. C.), (1993), 39(8), 1705–12., Nov. 22, 1993.

Jones et al. (CA 102:41075 abstract of J. Anal. Toxicol. (1984), 8(6), 252–4 Apr. 4, 1985.

Defaye, Genevieve, (CA 72:79254 abstract of Publ. Sci. Tech. Min. Air (Fr.), Notes Tech. (1969, No. N. T. 165,78 pages), Apr. 13, 1970.

Matsumoto et al. (CA 77:126882 abstract of Chem. Lett. (1972), (7), 581–6., Nov. 6, 1972.

S. H. Burstein et al., "Synthetic Nonpyschotropic Cannabinoids With Potent Antiinflammatory, Analgesic, and Leukocyte Antiadhesion Activities", *J. Medicinal Chem.*, 35(17):3135–3136 (1992).

L. S. Melvin et al., "A Cannabinoid Derived Prototypical Analgesic," *J. Med. Chem.*, 1984, 27:67–71.

*Primary Examiner*—Sabiha N. Qazi
*Attorney, Agent, or Firm*—Pennie & Edmonds LLP

[57] ABSTRACT

The present invention relates to non-psychoactive derivatives of tetrahydro-cannabinol, which exhibit anti-inflammatory, analgesic and leukocyte antiadhesion activities. The invention includes novel derivatives of (3R,4R)-$\Delta^8$-tetrahydrocannabinol-11-oic acids [hereinafter referred to as (3R,4R)-$\Delta^8$-THC-11-oic acid], as well as pharmaceutical compositions containing the (3R,4R)-$\Delta^8$-THC-11-oic acid derivatives. The invention further covers methods of administering the novel derivatives and pharmaceutical compositions as therapeutic agents in the treatment of pain and tissue inflammation. Non-psychoactive derivatives of $\Delta^8$-THC-11-oic acid are described which have analgesic and anti-inflammatory properties.

19 Claims, 2 Drawing Sheets

(3R,4R)-Δ⁸-TETRAHYDROCANNABINOL-11-OIC ACIDS USEFUL AS ANTIINFLAMMATORY AGENTS AND ANALGESICS

TECHNICAL FIELD

The present invention relates to non-psychoactive derivatives of tetrahydro-cannabinol, which exhibit anti-inflammatory, analgesic and leukocyte anti-adhesion activities. The invention includes novel derivatives of (3R,4R)-$\Delta^8$-tetrahydrocannabinol-11-oic acids [hereinafter referred to as (3R,4R)-$\Delta^8$-THC-11-oic acid], as well as pharmaceutical compositions containing the (3R,4R)-$\Delta^8$-THC-11-oic acid derivatives. The invention further includes methods of administering the novel derivatives and pharmaceutical compositions as therapeutic agents in the treatment of pain, tissue inflammation, leukocyte anti-adhesion activity, and the like.

BACKGROUND OF THE INVENTION $\Delta^9$-Tetrahydrocannabinol [THC], depicted in Formula I under alternate numbering systems, is the major psychoactive constituent of marijuana.

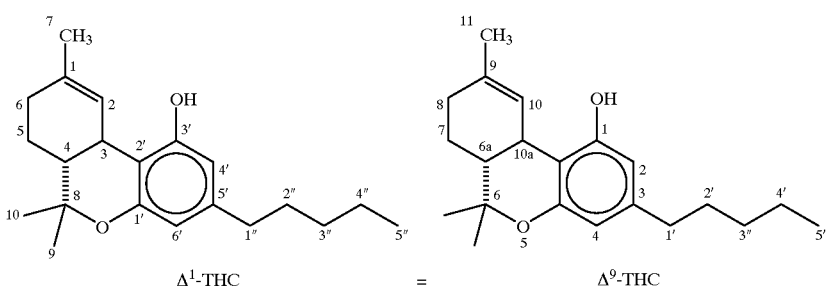

Formula I

In addition to mood-altering effects, THC has been reported to exhibit other activities, some of which may have therapeutic value. The potential therapeutic value of THC has led to a search for related compounds which, while devoid of psychoactive effects, retain the activities of potential medicinal value.

Previous work with $\Delta^8$-Tetrahydrocannabinol [(3R,4R) 6a,7,10,10a-tetrahydro-6,6,9-trimethyl-3-pentyl-6H-dibenzo[b,d]pyran-1-ol, hereinafter referred to as $\Delta^8$-THC], which is depicted in Formula II below, has indicated that certain derivatives of this compound depicted in Formula II below, may prove clinically useful. The 11-carboxy derivative of $\Delta^8$-THC [$\Delta^8$-THC-11-oic acid] has been reported to be a non-psychoactive, potent antagonist to endogenous platelet activating factor and, thus, a useful treatment for PAF-induced disorders, such as asthma, systemic anaphylaxis, and septic shock. (U.S. Pat. No. 4,973,603, issued to the present inventor). Another derivative, (3S,4S)-11-hydroxy-$\Delta^8$-THC-1',1' dimethylheptyl essentially free of the (3R,4R) form, has been reported to possess analgesic and anti-emetic activities. (U.S. Pat. No. 4,876,276).

U.S. Pat. No. 4,847,290, issued to the present inventor, discloses a method of relieving pain in mammals by administering an effective analgesic amount of $\Delta^9$-THC-11-oic acid or an analog thereof. These THC derivatives are disclosed to be non-psychoactive metabolites.

U.S. Pat. No. 5,338,753, also issued to the present inventor, discloses (3R,4R)-$\Delta^8$-Tetrahydrocannabinol-11-oic acid derivatives having Formula II below:

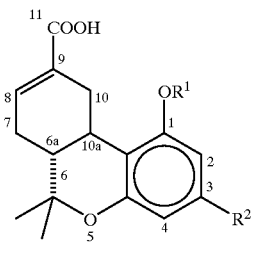

Formula II wherein $R^1$ is a hydrogen atom, $-COCH_3$ or $-COCH_2CH_3$; $R^2$ is a straight chain or branched $C_5$-$C_{12}$ alkyl, which may have a terminal aromatic ring; a group $-(CH_2)_m-O-R^3$, wherein m is an integer from 0 to 7 and $R^3$ is a straight chain or branched alkyl group containing from 1 to 12 carbon atoms, which may have a terminal aromatic ring; or a group $CH-(CH_3)-(CH_2)_n-O-R^4$, wherein n is an integer from 0 to 7 and $R^4$ is a straight chain or branched alkyl containing from 1 to 12 carbon atoms, which may have a terminal aromatic ring. These $\Delta^8$-THC-11-oic acid derivatives are also discussed in an article by Sumner H. Burstein, et al., entitled "Synthetic Nonpsychotropic Cannabinoids with Potent Antiinflammatory, Analgesic, and Leukocyte Antiadhesion Activities." [*J. Medicinal Chem.*, 35(17):3135–3136 (1992).

It is desired, however, to obtain compounds, pharmaceutical compositions, and methods of treatment using compounds substantially devoid of psychoactive effect and with improved therapeutic effects compared to those achieved by conventional $\Delta^8$-THC-11-oic acid derivatives, such as those described above. The present invention advantageously affords such compounds, pharmaceutical compositions, and methods of treatment using the compounds and compositions.

SUMMARY OF THE INVENTION

The present invention relates to a compound having the formula:

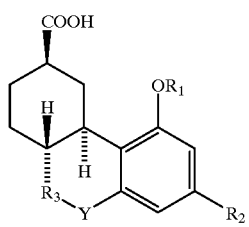

Formula III wherein $R^1$ is hydrogen, —$COCH_3$, or —$COCH_2CH_3$; $R_2$ is a branched $C_{5-12}$alkyl compound which may have a terminal aromatic ring, or a branched —$OCHCH_3(CH_2)_m$alkyl compound which may have a terminal aromatic ring, wherein m is 0 to 7; $R_3$ is hydrogen, a $C_{1-8}$alkyl compound, or a $C_{1-8}$alkanol compound; and Y is nil or a bridging group of NH or oxygen; provided that where Y is oxygen and $R_2$ is a branched $C_{5-12}$alkyl compound, $R_3$ is not —$CHCH_3$.

In one preferred embodiment, $R_1$ is hydrogen, $R_2$ is 1',1'-dimethylheptyl, and Y is nil. In another preferred embodiment, $R_2$ is a branched —$O(CHCH_3)(CH_2)_m$alkyl compound terminated with a phenyl ring, wherein m is 0 to 7, and $R_3$ is —$CHCH_3$. This embodiment includes the stereoisomers of such compounds, as well as a racemic mixture or any other percentage mixture of the stereoisomers between 0 and 100 weight percent.

The invention also relates to pharmaceutical compositions that include the compound and its two preferred embodiments described above.

The invention further relates to methods of relieving pain in a mammal by administering to the mammal a therapeutically effective analgesic amount of the compound or pharmaceutical composition, or either of the preferred embodiments, described above.

The invention also relates to methods of relieving inflammation of bodily tissue of a mammal by administering to the mammal a therapeutically effective anti-inflammatory amount of the compound or pharmaceutical composition, or either of the preferred embodiments, described above.

DETAILED DESCRIPTION OF THE INVENTION

Figure 1:
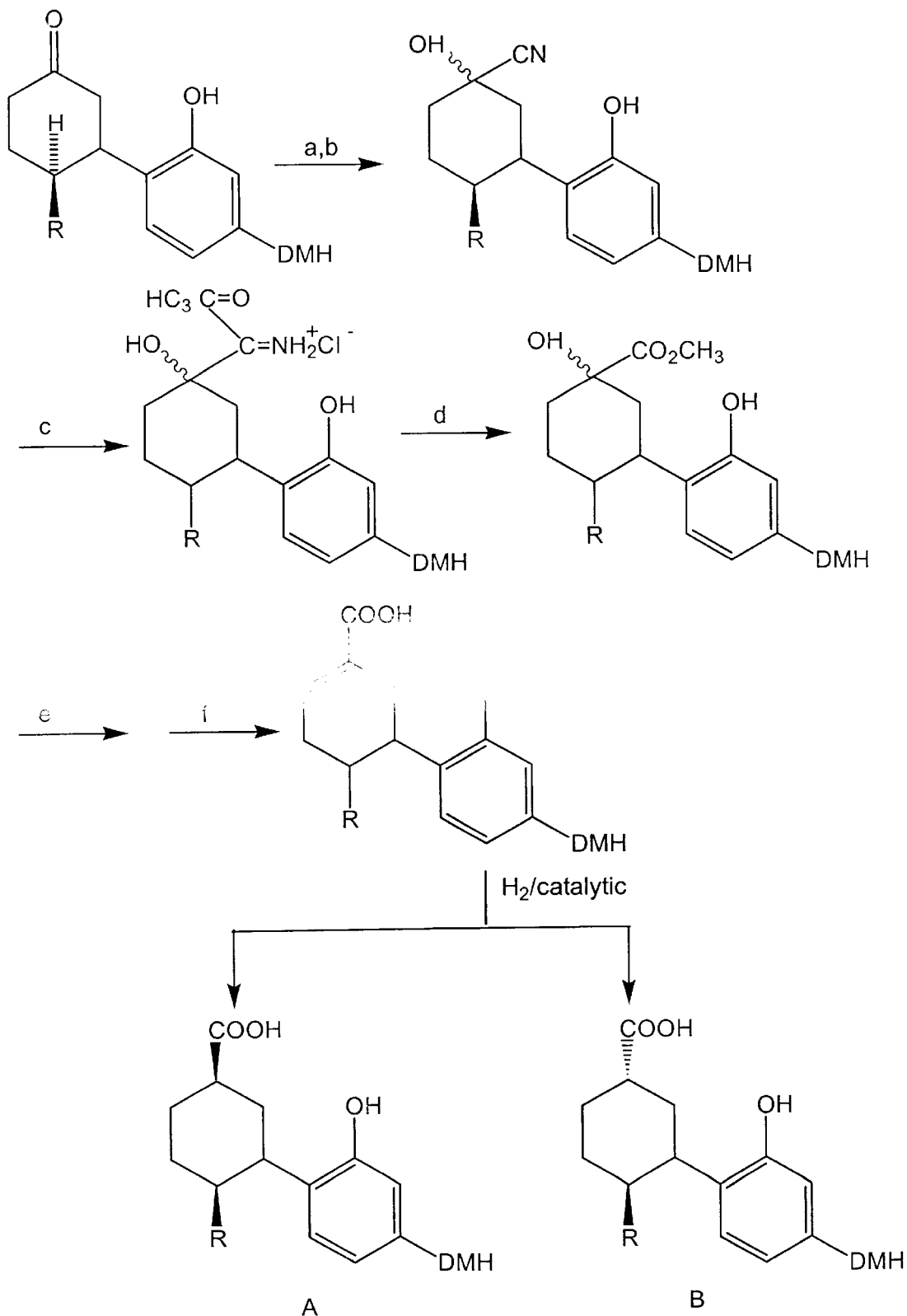
FIG. 1 illustrates a synthetic scheme for the preparation of the $\Delta^8$-THC-11-oic acid derivatives according to the present invention.

The present invention relates to (3R,4R)-$\Delta^8$-Tetrahydrocannabinol-11-oic acid derivatives depicted in Formula III below:

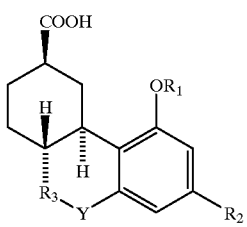

Formula III wherein $R^1$ is hydrogen, —$COCH_3$, or —$COCH_2CH_3$; $R_2$ is a branched $C_{5-12}$alkyl compound which may have a terminal aromatic ring, or a branched —$OCHCH_3(CH_2)_m$alkyl compound which may have a terminal aromatic ring, wherein m is 0 to 7; $R_3$ is hydrogen, a $C_{1-8}$alkyl compound, or a $C_{1-8}$alkanol compound; and Y is nil or a bridging group of NH or oxygen; provided that where Y is oxygen and $R_2$ is a branched $C_{5-12}$alkyl compound, $R_3$ is not —$CHCH_3$.

Preferred compounds are obtained when $R_1$ is hydrogen, $R_2$ is 1',1'-dimethylheptyl, and Y is nil. Thus, in this preferred form, the compounds have Formula IV below:

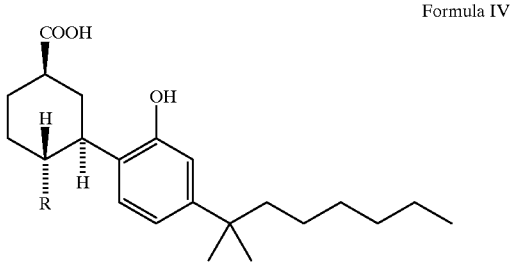

Formula IV

In these compounds, R includes hydrogen, branched or unbranched $C_{1-8}$alkyl compounds, and branched or unbranched $C_{1-8}$alkanol compounds. In a more preferred form, R is methyl or methanol, or a branched or unbranched ethyl, propyl, ethanol, or propanol.

Preferred compounds are also obtained when $R_2$ is a branched —$OCHCH_3(CH_2)_m$alkyl compound terminated with a phenyl ring, wherein m is 0 to 7, Y is NH or oxygen, and $R_3$ is —$CHCH_3$. More preferred compounds include those where m is 3, and these compounds have Formula V below:

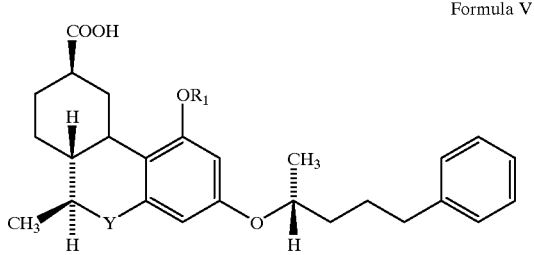

Formula V

In the preferred compounds, $R_1$ is hydrogen, —$COCH_3$, or —$COCH_2CH_3$, and more preferably $R_1$ is hydrogen.

The preferred and more preferred compounds are also similarly preferred when used in pharmaceutical compositions and for methods of eliciting an analgesic effect and treating tissue inflammation and leukocyte anti-adhesion activity by administration of a compound or pharmaceutical composition according to the invention.

The phrase "therapeutically effective amount," "therapeutically effective analgesic amount," or "therapeutically effective anti-inflammatory amount" means that amount of the pharmaceutical composition that provides a therapeutic benefit in the treatment, prevention, or management of pain, tissue inflammation, and leukocyte anti-adhesion activity.

The compositions of the present invention can be used in both veterinary medicine and human therapy. The magnitude of a prophylactic or therapeutic dose of the composition in the acute or chronic management of pain, tissue inflammation or leukocyte anti-adhesion activity will vary with the severity of the condition to be treated and the route of administration. The dose, and perhaps the dose frequency, will also vary according to the age, body weight, and response of the individual patient. In general, the total daily dose range of the active ingredient of this invention is generally between about 10 and 500 mg per 70 kg of body weight per day, preferably between about 50 and 250 mg per 70 kg of body weight per day, and more preferably between about 100 and 150 mg per 70 kg of body weight per day. The actual preferred amounts of the active ingredient will vary with each case, according to the species of mammal, the nature and severity of affliction being treated, and the method of administration. In general, the compositions of the present invention are periodically administered to an individual patient as necessary to improve symptoms of the disease being treated. The length of time during which the compositions are administered and the total dosage will necessarily vary with each case, according to the nature and severity of the affliction being treated and the physical condition of the subject.

Generally, then, each daily dose is a unit dose, i.e., tablet, cachet or capsule, which contains between about 10 mg to 700 mg of the active ingredient, or pharmaceutical composition, preferably about 50 mg to 250 mg, and more preferably about 100 mg to 150 mg of the active ingredient (i.e., excluding excipients and carriers). If desired, the daily dose may include two or more unit doses, i.e., tablets, cachets or capsules, to be administered each day.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The term "unit dose" is meant to describe a single dose, although a unit dose may be divided, if desired. Although any suitable route of administration may be employed for providing the patient with an effective dosage of the composition according to the methods of the present invention, oral administration is preferred. Suitable routes include, for example, oral, rectal, parenteral (e.g., in saline solution), intravenous, topical, transdermal, subcutaneous, intramuscular, by inhalation, and like forms of administration may be employed. Suitable dosage forms include tablets, troches, dispersions, suspensions, solutions, capsules, patches, suppositories, and the like, although oral dosage forms are preferred.

The pharmaceutical compositions used in the methods of the present invention include the active ingredients described above, and may also contain pharmaceutically acceptable carriers, excipients and the like, and optionally, other therapeutic ingredients. In one embodiment, for example, the drug is dissolved in a vegetable oil, such as olive oil or peanut oil, and, optionally, encapsulated in a gelatin capsule. For human therapy, a preferred method of administering compounds or pharmaceutical compositions having Formula III, IV, or V is orally, in the form of a gelatin capsule.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

The compositions for use in the methods of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are capsules.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, as creams, pastes, gels, or ointments, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier with the active ingredient which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form, such as powder or granules, optionally mixed with a binder (e.g., carboxymethylcellulose, gum arabic, gelatin), filler (e.g., lactose), adjuvant, flavoring agent, coloring agent, lubricant, inert diluent, coating material (e.g., wax or plasticizer), and a surface active or dispersing agent. Molded tablets may be made by molding, in a suitable machine, a mixture of the powdered compound moistened with an inert liquid diluent. Those skilled in the art will know, or will be able to ascertain with no more than routine experimentation, appropriate pharmacological carriers for said pharmaceutical compositions.

EXAMPLES

The invention is further defined by reference to the following examples describing in detail the preparation of the compound and the compositions used in the methods of the present invention, as well as their utility. The examples are representative, and they should not be construed to limit the scope of the invention.

Examples 1–2

Preparation of Derivatives

Figure 2:
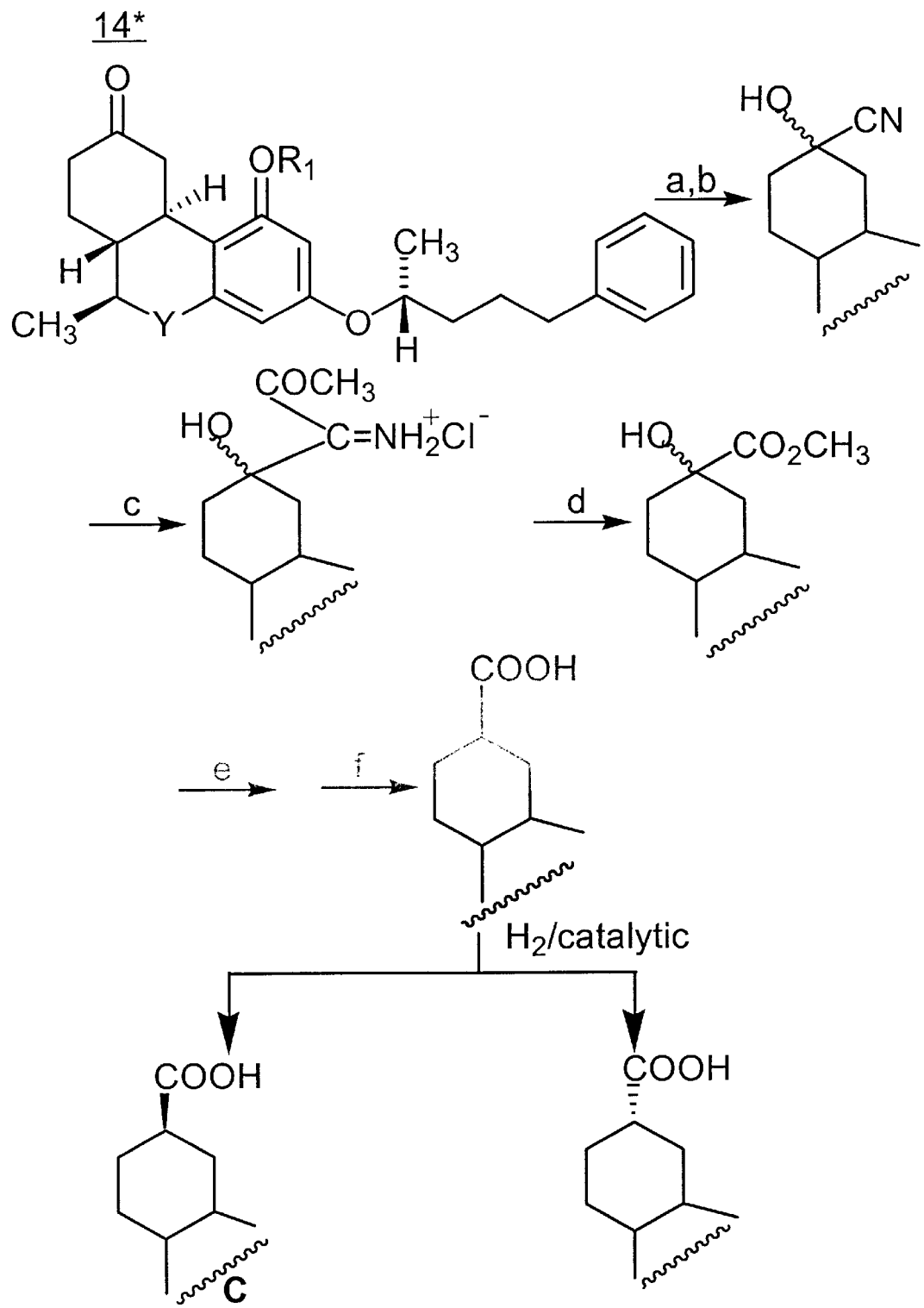
FIG. 2 illustrates an alternative synthetic scheme for the preparation of the $\Delta^8$-THC-11-oic acid derivatives according to the present invention.

The compounds of Formula III may be prepared according to the synthetic schemes depicted in FIGS. 1 and 2. FIG. 1 depicts a scheme to produce compounds of Formula IV, and FIG. 2 depicts a scheme to produce compounds of Formula V. DMH is dimethylheptyl in the figures, where 1',1'-dimethylheptyl is used in the preparation of the compounds and compositions of the present invention. The intermediates and final compounds in these schemes are generally prepared by the methods disclosed in Schwartz, A., and Madan, P., *J. Org. Chem.*, 51:5463–5465 (1986), which is expressly incorporated by reference thereto for the purpose of teaching a skilled artisan how to prepare the compounds of the present invention.

In general, melting points are taken in glass capillary tubes with a Thomas-Hoover Uni-Melt apparatus. Infrared spectra are recorded on a JASCO A-200 spectrophotometer. Rotations are determined on a Perkin-Elmer Model 141 polarimeter in chloroform. Chromatographic separations are performed on silica gel columns (Woelm TSC silica, for dry chromatography, activity III/30 mm, No. 04530). The high-resolution mass spectrometry (HRMS) is performed on a Varian 711 instrument.

1. Preparation of (trans-R,R & S,S)-6a,7,8,9,10,10a-Hexahydro-1,9dihydroxy-6aR-3-DMH-dibenzo[b,d]-pyran-9-carbonitrile—Step a,b A solution of 5 g (0.016 mol) of the DMH-substituted compound shown at the top of FIG. 1 in 175 mL methanol is added to a suspension of 5 g (0.10 mol) of sodium cyanide in 20 mL of methanol, and the resulting mixture is stirred at room temperature under nitrogen for 2 hrs.

To this mixture is added 5.75 mL of glacial acetic acid in 50 mL of methanol, and stirring is continued for 0.5 hrs. The pH of the mixture is adjusted to about 2 with anhydrous HCl (g), and the mixture is stirred overnight under nitrogen, whereupon the solvent is removed by using a 40° C. water bath and an aspirator. The residue is dissolved into 75 mL of water and extracted with 2×100 mL of methylene chloride. The combined organic layers are dried ($Na_2SO_4$) and the solvent is concentrated to dryness, first on a rotary evaporator at 40° C. (20 mm) and finally for 0.5 hrs. at 0.5 mm, to afford the a,b-product compound as a light yellow foam, used without further purification in the next step. An analytical sample is prepared by recrystallization from $CH_2Cl_2$/petroleum ether to give colorless needles.

2. Preparation of (trans-R,R & S,S)-6a,7,8,9,10,10a-Hexahydro-1,9-dihydroxy-6aR-3-DMH-dibenzo[b,d]-pyran-9-carboxylic acid methyl ester—Step d Anhydrous HCl (g) is bubbled into a stirred solution of about 5.5 g of the a,b-product compound in 150 mL methanol at 3° C. (ice bath) over a period of 1.25 hrs. to saturation. The flask is capped with a septum and kept in the freezer (−20° C.) for 72 hrs.

To this mixture is added 75 mL of 6N aqueous HCl, and the solvent is concentrated to dryness, first on a rotary evaporator (35° C. at 20 mm) and finally at 0.5 mm to afford an oil that is suspended in 150 mL of 50% aqueous methanol. A copious white precipitate is formed on standing at room temperature overnight. The solids are collected by filtration and then dissolved in 250 mL of ethyl acetate. A small amount of water is separated and the organic layer dried ($Na_2SO_4$) and concentrated to dryness in vacuo (30° C. at 20 mm).

The residue is triturated with 50 mL of petroleum ether (bp 30–60° C.). The solids are collected by filtration, washed with 50 mL of petroleum ether, and then dried in vacuo (0.5 mm) for 2 hrs. to afford 3.1 g of the compound as a colorless solid. The mother liquors are concentrated to give 1.3 g of a yellow oil, which, when analyzed, indicates the epimeric hydroxy ester of the d-product compound.

3. Preparation of (trans-R,R & S,S)-6a,7,10,10a-Tetrahydro-1-hydroxy-6aR-3-DMH-dibenzo[b,d]-pyran-9-carboxylic acid methyl ester—Step e A 50 mL reaction flask equipped with a nitrogen bubbler and a magnetic stirrer are charged with 1.4 g of the above d-product compound, 10 mL of pyridine, and 2.0 mL of thionyl chloride, and then the reaction mixture is stirred at room temperature under nitrogen for 1 hr. This mixture is quenched by pouring into 30 mL of ice water and extracted into 3×30 mL of ethyl acetate. The organic layer is dried ($Na_2SO_4$) and evaporated to dryness to afford about 1.2 g as a solidified foam. The foam is triturated with 30 mL of petroleum ether (30–60° C.) to afford 975 mg of the e-product compound as a light yellow solid.

4. Preparation of (trans-R,R & S,S)-6a,7,10,10a-Tetrahydro-6aR-3-DMH-dibenzo[b,d]-pyran-9-carboxylic acid—Step f A solution of 50 mL of MeOH and 15 mL of 1 N NaOH is placed in a 100-mL three-necked flask equipped with magnetic stirrer and bubbler and heated to reflux while Ar gas is passed through the solution for 30 min. via a gas dispersion tube. The tube is removed, 540 mg of the e-product compound above is added in one portion to the refluxing solution, and the resultant mixture (now green) is allowed to reflux for 2 hrs, after which TLC analysis in silica (EtOAc-hexanes, 1:1) indicate complete reaction. The reaction mixture is cooled to 5° C. (ice bath) and acidified with methanolic HCl to pH 1. The solvent is removed under vacuum, and the residue is dissolved in 25 mL of water, extracted into $CHCl_3$ (3×100 mL), and dried over $Na_2SO_4$. The solvent is removed under vacuum to give an oil, to which 25 mL of hexanes is added, and the solution is kept in a refrigerator 10° C. overnight. The resultant crystals are filtered to give about 490 mg of the f-product compound.

Following subsequent catalysis with hydrogen, the above f-product compound becomes the presently claimed invention, wherein the R is the $R_3$ group, where Y is nil.

The scheme in FIG. 2 permits preparation of the presently claimed compounds by use of the above procedure. In this manner, compounds where Y is oxygen or NH; where $R_3$ equals R equals —$CHCH_3$, and where $R_2$ is a branched —OCHCH$_3$(CH$_2$)$_m$alkyl compound which may have a terminal aromatic ring, wherein m is 0 to 7, may be prepared.

Example 3

Leukocyte Adhesion Test

Leukocytes are thought to be major contributors to the inflammatory response, and their ability, in this regard, is reflected by their adhesion to a variety of substrates. Following the procedure of Audette and Burstein (Audette, C. A., and Burstein, S., "Inhibition of Leukocyte Adhesion by the In Vivo and In Vitro Administration of Cannabinoids," *Life Sci.* 47:753–759 (1983), peritoneal cells from female CD-1 mice (20–25 g) are collected at ninety (90) minutes following oral administration of the test compound or vehicle (50 μL of peanut oil). Cells from each treatment group (N=3) are pooled, and equal numbers of cells are aliquoted into six culture dish wells (1.9 cm$^2$ area). After incubation for 18–20 hours, nonadhering cells are removed and the remaining cell monolayer quantitated by DNA measurement. Cell viability is monitored by Trypan Blue exclusion.

Example 4

Measurement of Cataleptic Effects

The cataleptic response in mice or other laboratory animals is measured using the ring test described by Pertwee. (Pertwee, R. G., "The Ring Test: A Quantitative Method of Assessing the Cataleptic Effect of Cannabis in Mice," *Br. J. Pharmacol.* 46:753–763 (1972)). Mice are placed on a horizontal wire ring 5.5 cm in diameter, which is attached to a 16 cm vertical rod. The hind paws and fore paws are placed at opposite sides of the ring. It is important that the ambient temperature be maintained at 30° C. and that the environment be free of auditory stimuli and bright lights. The response is calculated as the fraction of time the mouse is immobile over a five (5) minute test period. Measurements are done between a fixed time, e.g., 2 p.m. to 4 p.m.

Example 5

Paw Edema Test for Inflammation

The induction of paw edema, in rodents, by the injection of arachidonic acid, has been used as an experimental model for inflammation. (Calhoun W. et al. "Effect of Selected Antiinflammatory Agents and Other Drugs on Zymosan, Arachidonic Acid, PAF and Carrageenan Induced Paw Edema in the Mouse." *Agents Actions* 21:306–309 (1987)). Administration of non-steroidal anti-inflammatory drugs (NSAIDs) prior to induction with arachidonic acid, leads to a dose-related inhibition which may be considered predictive of clinical efficacy.

The conditions were as previously reported by Calhoun et al., and by Burstein et al. (Burstein S. et al. "Antagonism to the Actions of PAF by a Nonpsychoactive Cannabinoid." *J. Pharmacol. Exper. Ther.* 251:531–535 (1989)), with water being substituted for mercury as the displacement medium. PAF (1.0 μg) or arachidonic acid (1.0 mg) dissolved in 50 μL of 5% ethanol in saline, is injected subcutaneously into the plantar surface of the right hind paw of ether-anesthetized CD-1 female mice (20–25 g) obtained from Charles River Laboratories. The volume of the right foot is measured to the level of the lateral malleolus by water displacement before treatment, fifteen (15) minutes after PAF injection, or thirty (30) minutes after arachidonic acid injection. The change in paw volume is calculated for each mouse and the significance for each group is determined by a paired t test. The compounds of the present invention are then tested to determine efficacy in reducing arachidonate-induced paw edema.

Example 6

Hot Plate Test for Antinociception

The hot-plate test is a method for measuring the analgesic activity of pharmacologic agents based on the reaction time of mice to lick their forepaws and/or jump after being placed on an aluminum hot plate heated to, and maintained at, 54–56° C. (Kitchen I and Green PG. "Differential Effects of DFP Poisoning and Its Treatment on Opioid Antinociception in the Mouse." *Life Sci.* 33:669-14 672 (1983).

An aluminum surface is maintained at 55±1° C. by circulating water through the passages in the metal. A clear plastic cylinder, 18 cm in diameter and 26 cm high, is placed on the surface to prevent escape. The end point is taken when the mouse either performed a hind paw lick or jumped off the surface; in no case are the animals kept more than 30 seconds on the plate. Mice are never used more than one time; control values are measured at 11 a.m. and test values at 2 p.m. The compounds to be tested are administered orally ninety (90) minutes before the hot plate test. The percent change in response time (latency) is calculated by comparing the mean of the control values with the mean of the test values and statistical significance determined by a paired t test.

Example 7

Preparation of Capsules

A large number of unit capsules are prepared by filling standard two-piece hard gelatin capsules each with the desired amount of powdered active ingredient as described above, 150 milligrams of lactose, 50 milligrams of cellulose, and 6 milligrams magnesium stearate.

Example 8

Preparation of Soft Gelatin Capsules

A mixture of active ingredient in a digestible oil such as soybean oil, lecithin, cottonseed oil or olive oil is prepared and injected by means of a positive displacement pump into gelatin to form soft gelatin capsules containing the desired amount of the active ingredient. The capsules are washed and dried for packaging.

Examples 9–23

Various Compounds of the Invention

Various compounds of the present invention may be prepared, for example, according to Examples 1 and 2 above. The following table illustrates various specific embodiments of the compounds of Formula III of the present invention. When Y is nil, R equals R$_3$ in the table below.

| Example | $R_1$ | $R_2$ | $R_3$ | Y |
|---|---|---|---|---|
| 7 | hydrogen | DMH | hydrogen | nil |
| 8 | hydrogen | DMH | $CH_3$— | nil |
| 9 | hydrogen | DMH | $CH_3CH_2$— | nil |
| 10 | hydrogen | DMH | $CH_3CH_2CH_2$— | nil |
| 11 | hydrogen | DMH | —$CH_2OH$ | nil |
| 12 | hydrogen | DMH | —$(CH_2)_2OH$ | nil |
| 13 | hydrogen | DMH | —$(CH_2)_3OH$ | nil |
| 14 | hydrogen | DMH | —$(CH_2)_4OH$ | nil |
| 15 | hydrogen | DMH | —$(CH_2)_5OH$ | nil |
| 16 | hydrogen | —$OCHCH_3(CH_2)_3Ph$ | —$CHCH_3$ | oxygen |
| 17 | —$COCH_3$ | —$OCHCH_3(CH_2)_3Ph$ | —$CHCH_3$ | oxygen |
| 18 | —$COCH_2CH_3$ | —$OCHCH_3(CH_2)_3Ph$ | —$CHCH_3$ | oxygen |
| 19 | hydrogen | —$OCHCH_3(CH_2)_3Ph$ | —$CHCH_3$ | NH |
| 20 | —$COCH_3$ | —$OCHCH_3(CH_2)_3Ph$ | —$CHCH_3$ | NH |
| 21 | —$COCH_2CH_3$ | —$OCHCH_3(CH_2)_3Ph$ | —$CHCH_3$ | NH |

DMH = 1',1'-dimethylheptyl; Ph = Phenyl

Those skilled in the pharmaceutical art will recognize, or be able to ascertain using no more than routine experimentation, many equivalents to the specific embodiments of the invention described herein. Such equivalents are intended to be encompassed by the following claims.

What is claimed is:

1. A compound having the formula:

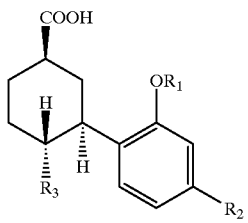

wherein $R_1$ is hydrogen, —$COCH_3$, or —$COCH_2CH_3$; $R_2$ is a branched $C_{5-12}$alkyl group which may have a terminal aromatic ring, or a branched —$OCHCH_3(CH_2)_m$alkyl group which may have a terminal aromatic ring, wherein m is 0 to 7; and $R_3$ is hydrogen, a $C_{1-8}$alkyl group, or a $C_{1-8}$alkanol group.

2. A compound according to claim 1, wherein $R_1$ is hydrogen, and $R_2$ is 1',1'-dimethylheptyl.

3. A compound according to claim 1, wherein $R_2$ is a branched —$OCHCH_3(CH_2)_m$alkyl group terminated with a phenyl ring, wherein m is 0 to 7, and $R_3$ is —$CHCH_3$.

4. A pharmaceutical composition comprising a therapeutically effective amount of the compound of claim 1.

5. A pharmaceutical composition comprising a therapeutically effective amount of the compound of claim 2.

6. A pharmaceutical composition comprising a therapeutically effective amount of the compound of claim 3.

7. A method of relieving pain in a mammal which comprises administering to the mammal a therapeutically effective analgesic amount of a compound according to claim 1.

8. A method of relieving pain in a mammal which comprises administering to the mammal a therapeutically effective analgesic amount of a pharmaceutical composition according to claim 4.

9. A method for relieving pain in an animal which comprises administering to the mammal a therapeutically effective analgesic amount of a compound according to claim 2.

10. A method of relieving pain in a mammal which comprises administering to the mammal a therapeutically effective analgesic amount of a pharmaceutical composition according to claim 5.

11. A method of relieving pain in a mammal which comprises administering to the mammal a therapeutically effective analgesic amount of a compound according to claim 3.

12. A method of relieving pain in a mammal which comprises administering to the mammal a therapeutically effective analgesic amount of a pharmaceutical composition according to claim 6.

13. A method of relieving inflammation of bodily tissue of a mammal which comprises administering to the mammal a therapeutically effective anti-inflammatory amount of a compound according to claim 1.

14. A method of relieving inflammation of bodily tissue of a mammal which comprises administering to the mammal a therapeutically effective anti-inflammatory amount of a pharmaceutical composition according to claim 4.

15. A method of relieving inflammation of bodily tissue of a mammal which comprises administering to the mammal a therapeutically effective anti-inflammatory amount of a compound according to claim 2.

16. A method of relieving inflammation of bodily tissue of a mammal which comprises administering to the mammal a therapeutically effective anti-inflammatory amount of a pharmaceutical composition according to claim 5.

17. A method of relieving inflammation of bodily tissue of a mammal which comprises administering to the mammal a therapeutically effective anti-inflammatory amount of a compound according to claim 3.

18. A method of relieving inflammation of bodily tissue of a mammal which comprises administering to the mammal a therapeutically effective anti-inflammatory amount of a pharmaceutical composition according to claim 6.

19. A pharmaceutical composition comprising a therapeutically effective amount of the compound of claim 1.

* * * * *